United States Patent [19]

Foster et al.

[11] Patent Number: 5,302,529

[45] Date of Patent: * Apr. 12, 1994

[54] PLASMID CODING FOR HUMAN PROTEIN C

[75] Inventors: Donald C. Foster, Seattle; Earl W. Davie, Bellevue, both of Wash.

[73] Assignee: The Board of Regents of the University of Washington, Seattle, Wash.

[*] Notice: The portion of the term of this patent subsequent to Nov. 6, 2007 has been disclaimed.

[21] Appl. No.: 512,961

[22] Filed: Apr. 23, 1990

Related U.S. Application Data

[63] Continuation of Ser. No. 766,109, Aug. 15, 1985, Pat. No. 4,968,626.

[51] Int. Cl.$^5$ ............................................. C12N 15/73
[52] U.S. Cl. .................................................. 435/320.1
[58] Field of Search ............... 536/27; 435/172.3, 226, 435/235, 320, 320.1; 935/14

[56] References Cited

U.S. PATENT DOCUMENTS

| | | | |
|---|---|---|---|
| 4,775,624 | 2/1985 | Bang et al. | 435/236 |
| 4,784,950 | 11/1988 | Hagen et al. | 435/69.1 |
| 4,968,626 | 11/1990 | Foster et al. | 435/320.1 |

FOREIGN PATENT DOCUMENTS

| | | |
|---|---|---|
| 138222 | 4/1985 | European Pat. Off. . |
| WO85/00521 | 2/1985 | PCT Int'l Appl. . |

OTHER PUBLICATIONS

J. H. Griffin et al., "Deficiency of Protein C in congenital Thrombotic Disease", *J. Clin. Invest.* 68:1370-1373, 1981.

W. Kisiel, "Human Plasma Protein C", *J. Clin. Invest.* 64:761-769, 19979.

V. W. M. van Hinsbergh et al., "Activated Protein C Decreases Plasminogen Activator-Inhibitor Activity in Endothelial Cell-Conditioned Medium", *Blood* 65:444-451, Feb. 1985.

W. Kisiel et al., "Enzymological Aspects of Blood Coagulation", *Behring Inst. Mitt.* 73:29-42, 1983.

J. E. Gardiner and J. H. Griffin, "Human Protein C and Thromboembolic Disease", *Progress in Hematology*, 265-278, 1983.

Phillip C. Comp et al., "Generation of Fibrinolytic Activity by Infusion of Activated Protein C into Dogs", *J. Clin. Invest.* 68:1221-1228, 1981.

Y. Sakata et al., "Activated Protein C Stimulates the Fibrinolytic Activity of Cultured Endothelial Cells and Decreases Antiactivator Activity", *Proc. Acad. Sci. USA* 82:1121-1125, 1985.

A. Broekmans et àl., "Congenital Protein C Deficiency and Venous Thromboembolism", *The New England Journal of Medicine* 309:340-344, 1983.

U. Seligsohn et al., "Homozygous Protein C Deficiency Manifested by Massive Venous Thrombosis in the Newborn", *The New England Journal of Medicine* 310:559-562, 1984.

R. A. Marlar, "Mechanism of Action of Human Activated Protein C, a Thrombin-Dependent Anticoagulant Enzyme", *Blood* 59:1067-1072, 1982.

Kisiel and Davie, "Protein C", *Methods in Enzymology* 80:320-332, 1981.

Miletich and Broze, "Characterization of Monoclonal Antibody Specific for the Heavy Chain of Non-Activated Human Protein C", *Thrombosis* 305a:1123, Nov. 1983.

(List continued on next page.)

Primary Examiner—Richard A. Schwartz
Assistant Examiner—Dian Cook
Attorney, Agent, or Firm—Seed and Berry

[57] ABSTRACT

Genomic and cDNA sequences coding for a protein having substantially the same biological activity as human protein C are disclosed. Recombinant plasmids and bacteriophage transfer vectors incorporating these sequences are also disclosed.

4 Claims, 13 Drawing Sheets

OTHER PUBLICATIONS

Esmon et al., "Identification of an encothelial cell cofactor for thrombin-catalyzed activation of protein C", *Proc. Natl. Acad. Sci. (USA)* 78:2249-2252, 1981.

Kisiel et al., "Anticoagulant Properties of Bovine Plasma Protein C following Activation by Thrombin", *Biochem.* 16:5824-5831, 1977.

Long et al., "Cloning and sequencing of liver cDNA coding for bovine protein C", *Proc. Natl. Acad. Sci. (USA)* 81:5653-5656, 1984.

Walker et al., "The Inhibition Of Blood Coagulation By Activated Protein C Through The Selective Inactivation Of Activated Factor V", *Biochim. et Biophys. Acta* 571:333-342, 1979.

Katayama et al., "Comparison of amino acid sequence of bovine coagulation Factor IX (Christmas Factor) with that of other vitamin K-dependent plama proteins", *Proc. Natl. Acad Sci. (USA)* 76:4990-4994, 1979.

Kaufman and Sharp, "Construction of a Modular Dihydrofolate Reductase cDNA Gene: Analysis of Signals Utilized for Efficient Expression", *Mol. and Cell. Biol.* 2:1304-1319, 1982.

Kaufman, "Identification of the components necessary for adenovirus translational control and their utilization in cDNA expression vectors", *Proc. Natl. Acad. Sci (USA)* 82: 689-693, 1985.

Hermonat et al., "Use of adeno-associated virus as a mammalian DNA cloning vector: Transduction of neomycin resistance into mammalian tissue culture cells", *Proc. Natl. Acad. Sci. (USA)* 81: 6466-6470, 1984.

McMullen et al., "The Occurrence Of Hydroxyaspartic Acid In The Vitamin K-Dependent Blood Coagulation Zymogens", *Biochem. and Biophys. Res. Comm.* 115:8-14, 1983.

Ginsburg et al., "Human von Willebrand Factor (vWF): Isolation of Complementary DNA (cDNA) Clones and Chromosomal Localization", *Science* 228:1401-1406, 1985.

```
GGCCTAAAAC CACACAGGCC TGGCCTTGAG TCCTGGCTCT GCGAGTAATG CATGGATGTA    -901

AACATGGAGA CCCAGGACCT TGCCTCAGTC TTCCGAGTCT GGTGCCTGCA GTGTACTGAT    -841

GGTGTGAGAC CCTACTCCTG GAGGATGGGG GACAGAATCT GATCGATCCC CTGGGTTGGT    -781

GACTTCCCTG TGCAATCAAC GGAGACCAGC AAGGGTTGGA TTTTTAATAA ACCACTTAAC    -721

TCCTCCGAGT CTCAGTTTCC CCCTCTATGA AATGGGGTTG ACAGCATTAA TAACTACCTC    -661

TTGGGTGGTT GTGAGCCTTA ACTGAAGTCA TAATATCTCA TGTTTACTGA GCATGAGCTA    -601

TGTGCAAAGC CTGTTTTGAG AGCTTTATGT GGACTAACTC CTTTAATTCT CACAACACCC    -541

TTTAAGGCAC AGATACACCA CGTTATTCCA TCCATTTTAC AAATGAGGAA ACTGAGGCAT    -481

GGAGCAGTTA AGCATCTTGC CCAACATTGC CCTCCAGTAA GTGCTGGAGC TGGAATTTGC    -421

ACCGTGCAGT CTGGCTTCAT GGCCTGCCCT GTGAATCCTG TAAAAATTGT TTGAAAGACA    -361

CCATGAGTGT CCAATCAACG TTAGCTAATA TTCTCAGCCC AGTCATCAGA CCGGCAGAGG    -301

CAGCCACCCC ACTGTCCCCA GGGAGGACAC AAACATCCTG GCACCCTCTC CACTGCATTC    -241

TGGAGCTGCT TTCTAGGCAG GCAGTGTGAG CTCAGCCCCA CGTAGAGCGG GCAGCCGAGG    -181

CCTTCTGAGG CTATGTCTCT AGCGAACAAG GACCCTCAAT TCCAGCTTCC GCCTGACGGC    -121

CAGCACACAG GGACAGCCCT TTCATTCCGC TTCCACCTGG GGGTGCAGGC AGAGCAGCAG     -61

CGGGGGTAGC ACTGCCCGGA GCTCAGAAGT CCTCCTCAGA CAGGTGCCAG TGCCTCCAGA     -1

ATG TGG CAG CTC ACA AGC CTC CTG CTG TTC GTG GCC ACC TGG GGA ATT       48
Met Trp Gln Leu Thr Ser Leu Leu Leu Phe Val Ala Thr Trp Gly Ile
-42                                                         ▼
TCC GGC ACA CCA GCT CCT CTT GGTAAGGCCA CCCCACCCCT ACCCCGGGAC          99
Ser Gly Thr Pro Ala Pro Leu
               -20

CCTTGTGGCC TCTACAAGGC CCTGGTGGCA TCTGCCCAGG CCTTCACAGC TTCCACCATC    159

TCTCTGAGCC CTGGGTGAGG TGAGGGGCAG ATGGGAATGG CAGGAATCAA CTGACAAGTC    219

CCAGGTAGGC CAGCTGCCAG AGTGCCACAC AGGGGCTGCC AGGGCAGGCA TGCGTGATGG    279

CAGGGAGCCC CGCGATGACC TCCTAAAGCT CCCTCCTCCA CACGGGGATG GTCACAGAGT    339

CCCCTGGGCC TTCCCTCTCC ACCCACTCAC TCCCTCAACT GTGAAGACCC CAGGCCCAGG    399

CTACCGTCCA CACTATCCAG CACAGCCTCC CCTACTCAAA TGCACACTGG CCTCATGGCT    459

GCCCTGCCCC AACCCCTTTC CTGGTCTCCA CAGCCAACGG GAGGAGGCCA TGATTCTTGG    519
```

FIG. 2A

```
GGAGGTCCGC AGGCACATGG GCCCCTAAAG CCACACCAGG CTGTTGGTTT CATTTGTGCC      579
TTTATAGAGC TGTTTATCTG CTTGGGACCT GCACCTCCAC CCTTTCCCAA GGTGCCCTCA      639
GCTCAGGCAT ACCCTCCTCT AGGATGCCTT TTCCCCCATC CCTTCTTGCT CACACCCCCA      699
ACTTGATCTC TCCCTCCTAA CTGTGCCCTG CACCAAGACA GACACTTCAC AGAGCCCAGG      759
ACACACCTGG GGACCCTTCC TGGGTGATAG GTCTGTCTAT CCTCCAGGTG TCCCTGCCCA      819
AGGGGAGAAG CATGGGGAAT ACTTGGTTGG GGGAGGAAAG GAAGACTGGG GGGATGTGTC      879
AAGATGGGGC TGCATGTGGT GTACTGGCAG AAGAGTGAGA GGATTTAACT TGGCAGCCTT      939
TACAGCAGCA GCCAGGGCTT GAGTACTTAT CTCTGGGCCA GGCTGTATTG GATGTTTTAC      999
ATGACGGTCT CATCCCCATG TTTTTGGATG AGTAAATTGA ACCTTAGAAA GGTAAAGACA     1059
CTGGCTCAAG GTCACACAGA GATCGGGGTG GGGTTCACAG GGAGGCCTGT CCATCTCAGA     1119
GCAAGGCTTC GTCCTCCAAC TGCCATCTGC TTCCTGGGGA GGAAAAGAGC AGAGGACCCC     1179
TGCGCCAAGC CATGACCTAG AATTAGAATG AGTCTTGAGG GGGCGGAGAC AAGACCTTCC     1239
CAGGCTCTCC CAGCTCTGCT TCCTCAGACC CCCTCATGGC CCCAGCCCCT CTTAGGCCCC     1299
TCACCAAGGT GAGCTCCCCT CCCTCCAAAA CCA▼GAC TCA GTG TTC TCC AGC AGC     1353
                                    Asp Ser Val Phe Ser Ser Ser
                                    -19
```

```
GAG CGT GCC CAC CAG GTG CTG CGG ATC CGC AAA CGT GCC AAC TCC TTC      1401
Glu Arg Ala His Gln Val Leu Arg Ile Arg Lys Arg Ala Asn Ser Phe
                                                -1  +1

CTG GAG GAG CTC CGT CAC AGC AGC CTG GAG CGG GAG TGC ATA GAG GAG      1449
Leu Glu Glu Leu Arg His Ser Ser Leu Glu Arg Glu Cys Ile Glu Glu

ATC TGT GAC TTC GAG GAG GCC AAG GAA ATT TTC CAA AAT GTG GAT GAC      1497
Ile Cys Asp Phe Glu Glu Ala Lys Glu Ile Phe Gln Asn Val Asp Asp

ACA▼GTAAGGCCAC CATGGGTCCA GAGGATGAGG CTCAGGGGCG AGCTGGTAAC            1550
Thr
37
```

```
CAGCAGGGGC CTCGAGGAGC AGGTGGGGAC TCAATGCTGA GGCCCTCTTA GGAGTTGTGG     1610
GGGTGGCTGA GTGGAGCGAT TAGGATGCTG GCCCTATGAT GTCGGCCAGG CACATGTGAC     1670
TGCAAGAAAC AGAATTCAGG AAGAAGCTCC AGGAAAGAGT GTGGGGTGAC CCTAGGTGGG     1730
GACTCCCACA GCCACAGTGT AGGTGGTTCA GTCCACCCTC CAGCCACTGC TGAGCACCAC     1790
TGCCTCCCCG TCCCACCTCA CAAAGAGGGG ACCTAAAGAC CACCCTGCTT CCACCCATGC     1850
```

FIG. 2B

```
CTCTGCTGAT CAGGGTGTGT GTGTGACCGA AACTCACTTC TGTCCACATA AAATCGCTCA    1910
CTCTGTGCCT CACATCAAAG GGAGAAAATC TGATTGTTCA GGGGGTCGGA AGACAGGGTC    1970
TGTGTCCTAT TTGTCTAAGG GTCAGAGTCC TTTGGAGCCC CCAGAGTCCT GTGGACGTGG    2030
CCCTAGGTAG TAGGGTGAGC TTGGTAACGG GGCTGGCTTC CTGAGACAAG GCTCAGACCC    2090
GCTCTGTCCC TGGGGATCGC TTCAGCCACC AGGACCTGAA AATTGTGCAC GCCTGGGCCC    2150
CCTTCCAAGG CATCCAGGGA TGCTTTCCAG TGGAGGCTTT CAGGGCAGGA GACCCTCTGG    2210
CCTGCACCCT CTCTTGCCCT CAGCCTCCAC CTCCTTGACT GGACCCCCAT CTGGACCTCC    2270
ATCCCCACCA CCTCTTTCCC CAGTGGCCTC CCTGGCAGAC ACCACAGTGA CTTTCTGCAG    2330
GCACATATCT GATCACATCA AGTCCCCACC GTGCTCCCAC CTCACCCATG GTCTCTCAGC    2390
CCCAGCAGCC TTGGCTGGCC TCTCTGATGG AGCAGGCATC AGGCACAGGC CGTGGGTCTC    2450
AACGTGGGCT GGGTGGTCCT GGACCAGCAG CAGCCGCCGC AGCAGCAACC CTGGTACCTG    2510
GTTAGGAACG CAGACCCTCT GCCCCCATCC TCCCAACTCT GAAAAACACT GGCTTAGGGA    2570
AAGGCGCGAT GCTCAGGGGT CCCCCAAAGC CCGCAGGCAG AGGGAGTGAT GGGACTGGAA    2630
GGAGGCCGAG TGACTTGGTG AGGGATTCGG GTCCCTTGCA TGCAGAGGCT GCTGTGGGAG    2690
CGGACAGTCG CGAGAGCAGC ACTGCAGCTG CATGGGGAGA GGGTGTTGCT CCAGGGACGT    2750
GGGATGGAGG CTGGGCGCGG GCGGGTGGCG CTGGAGGGCG GGGGAGGGGC AGGGAGCACC    2810
AGCTCCTAGC AGCCAACGAC CATCGGGCGT CGATCCCTGT TTGTCTGGAA GCCCTCCCCT    2870
CCCCTGCCCG CTCACCCGCT GCCCTGCCCC ACCCGGGCGC GCCCCTCCGC ACACCGGCTG    2930
CAGGAGCCTG ACGCTGCCCG CTCTCTCCGC AG▼CTG GCC TTC TGG TCC AAG CAC    2983
                                    Leu Ala Phe Trp Ser Lys His
                                                 38
▼
GTC GGTGAGTGCG TTCTAGATCC CCGGCTGGAC TACCGGCGCC CGCGCCCCTC           3036
Val
45
                                                    ▼
GGGATCTCTG GCCGCTGACC CCCTACCCCG CCTTGTGTCG CA GAC GGT GAC CAG       3090
                                               Asp Gly Asp Gln
                                                       46
TGC TTG GTC TTG CCC TTG GAG CAC CCG TGC GCC AGC CTG TGC TGC GGG    3138
Cys Leu Val Leu Pro Leu Glu His Pro Cys Ala Ser Leu Cys Cys Gly

CAC GGC ACG TGC ATC GAC GGC ATC GGC AGC TTC AGC TGC GAC TGC CGC    3186
His Gly Thr Cys Ile Asp Gly Ile Gly Ser Phe Ser Cys Asp Cys Arg
```

*FIG. 2C*

```
AGC GGC TGG GAG GGC CGC TTC TGC CAG CGC GGTGAGGGGG AGAGGTGGAT      3236
Ser Gly Trp Glu Gly Arg Phe Cys Gln Arg
                                    91

GCTGGCGGGC GGCGGGGCGG GGCTGGGGCC GGGTTGGGGG CGCGGCACCA GCACCAGCTG  3296

CCCGCGCCCT CCCCTGCCCG CA GAG GTG AGC TTC CTC AAT TGC TCT CTG GAC  3348
                        Glu Val Ser Phe Leu Asn Cys Ser Leu Asp
                        92

AAC GGC GGC TGC ACG CAT TAC TGC CTA GAG GAG GTG GGC TGG CGG CGC   3396
Asn Gly Gly Cys Thr His Tyr Cys Leu Glu Glu Val Gly Trp Arg Arg

TGT AGC TGT GCG CCT GGC TAC AAG CTG GGG GAC GAC CTC CTG CAG TGT   3444
Cys Ser Cys Ala Pro Gly Tyr Lys Leu Gly Asp Asp Leu Leu Gln Cys

CAC CCC GCA GGTGAGAAGC CCCCAATACA TCGCCCAGGA ATCACGCTGG           3493
His Pro Ala
        136

GTGCGGGGTG GGCAGGCCCC TGACGGGCGC GGCGCGGGGG GCTCAGGAGG GTTTCTAGGG  3553
AGGGAGCGAG GAACAGAGTT GAGCCTTGGG GCAGCGGCAG ACGCGCCCAA CACCGGGGCC  3613
ACTGTTAGCG CAATCAGCCC GGGAGCTGGG CGCGCCCTCC GCTTTCCCTG CTTCCTTTCT  3673
TCCTGGCGTC CCCGCTTCCT CCGGGCGCCC CTGCGACCTG GGGCCACCTC CTGGAGCGCA  3733
AGCCCAGTGG TGGCTCCGCT CCCCAGTCTG AGCGTATCTG GGGCGAGGCG TGCAGCGTCC  3793
TCCTCCATGT AGCCTGGCTG CGTTTTCTC TGACGTTGTC CGGCGTGCAT CGCATTTCCC   3853
TCTTTACCCC CTTGCTTCCT TGAGGAGAGA ACAGAATCCC GATTCTGCCT TCTTCTATAT  3913
TTTCCTTTTT ATGCATTTTA ATCAAATTTA TATATGTATG AAACTTTAAA AATCAGAGTT  3973
TTACAACTCT TACACTTTCA GCATGCTGTT CCTTGGCATG GTCCTTTTT TCATTCATTT   4033
TCATAAAAGG TGGACCCTTT TAATGTGGAA ATTCCTATCT TCTGCCTCTA GGGCATTTAT  4093
CACTTATTTC TTCTACAATC TCCCCTTTAC TTCCTCTATT TTCTCTTTCT GGACCTCCCA  4153
TTATTCAGAC CTCTTTCCTC TAGTTTTATT GTCTCTTCTA TTTCCCATCT CTTTGACTTT  4213
GTGTTTTCTT TCAGGGAACT TTCTTTTTTT TCTTTTTTTT TGAGATGGAG TTTCACTCTT  4273
GTTGTCCCAG GCTGGAGTGC AATGACGTGA TCTCAGCTCA CCACAACCTC CGCCTCCTGG  4333
ATTCAAGCGA TTCTCCTGCC GCAGCCTCCC GAGTAGCTGG GATTACAGGC ATGCGCCACC  4393
ACGCCCAGCT AATTTTGTGT TTTTAGTAGA GAAGGGGTTT CTCCGTGTTG GTCAAGCTGG  4453
```

*FIG. 2D*

```
TCTTGAACTC CTGACCTCAG GTGATCCACC TGCCTTGGCC TCCTAAAGTG CTGGGATTAC    4513
AGGCGTGAGC CACCGCGCCC AGCCTCTTTC AGGGAACTTT CTACAACTTT ATAATTCAAT    4573
TCTTCTGCAG AAAAAAATTT TTGGCCAGGC TCAGTAGCTC AGACCAATAA TTCCAGCACT    4633
TTGAGAGGCT GAGGTGGGAG GATTGCTTGA GCTTGGGAGT TTGAGACTAG CCTGGGCAAC    4693
ACAGTGAGAC CCTGTCTCTA TTTTTAAAAA AAGTAAAAAA AGATCTAAAA ATTTAACTTT    4753
TTATTTTGAA ATAATTAGAT ATTTCCAGGA AGCTGCAAAG AAATGCCTGG TGGGCCTGTT    4813
GGCTGTGGGT TTCCTGCAAG GCCGTGGGAA GGCCCTGTCA TTGGCAGAAC CCCAGATCGT    4873
GAGGGCTTTC CTTTTAGGCT GCTTTCTAAG AGGACTCCTC CAAGCTCTTG GAGGATGGAA    4933
GACGCTCACC CATGGTGTTC GGCCCCTCAG AGCAGGGTGG GGCAGGGGAG CTGGTGCCTG    4993
TGCAGGCTGT GGACATTTGC ATGACTCCCT GTGGTCAGCT AAGAGCACCA CTCCTTCCTG    5053
AAGCGGGGCC TGAAGTCCCT AGTCAGAGCC TCTGGTTCAC CTTCTGCAGG CAGGGAGAGG    5113
GGAGTCAAGT CAGTGAGGAG GGCTTTCGCA GTTTCTCTTA CAAACTCTCA ACATGCCCTC    5173
CCACCTGCAC TGCCTTCCTG GAAGCCCCAC AGCCTCCTAT GGTTCCGTGG TCCAGTCCTT    5233
CAGCTTCTGG GCGCCCCCAT CACGGGCTGA GATTTTTGCT TTCCAGTCTG CCAAGTCAGT    5293
TACTGTGTCC ATCCATCTGC TGTCAGCTTC TGGAATTGTT GCTGTTGTGC CCTTTCCATT    5353
CTTTTGTTAT GATGCAGCTC CCCTGCTGAC GACGTCCCAT TGCTCTTTTA AGTCTAGATA    5413
TCTGGACTGG GCATTCAAGG CCCATTTTGA GCAGAGTCGG GCTGACCTTT CAGCCCTCAG    5473
TTCTCCATGG AGTATGCGCT CTCTTCTTGG CAGGGAGGCC TCACAAACAT GCCATGCCTA    5533
TTGTAGGAGC TCTCCAAGAA TGCTCACCTC CTTCTCCCTG TAATTCCTTT CCTCTGTGAG    5593
GAGCTCAGCA GCATCCCATT ATGAGACCTT ACTAATCCCA GGGATCACCC CCAACAGCCC    5653
TGGGGTACAA TGAGCTTTTA AGAAGTTTAA CCACCTATGT AAGGAGACAC AGGCAGTGGG    5713
CGATGCTGCC TGGCCTGACT CTTGCCATTG GGTGGTACTG TTTGTTGACT GACTGACTGA    5773
CTGACTGGAG GGGGTTTGTA ATTTGTATCT CAGGGATTAC CCCCAACAGC CCTGGGGTAC    5833
AATGAGCCTT CAAGAAGTTT AACAACCTAT GTAAGGACAC ACAGCCAGTG GGTGATGCTG    5893
CCTGGTCTGA CTCTTGCCAT TCAGTGGCAC TGTTTGTTGA CTGACTGACT GACTGACTGG    5953
CTGACTGGAG GGGGTTCATA GCTAATATTA ATGGAGTGGT CTAAGTATCA TTGGTTCCTT    6013
GAACCCTGCA CTGTGGCAAA GTGGCCCACA GGCTGGAGGA GGACCAAGAC AGGAGGGCAG    6073
```

FIG. 2E

```
TCTCGGGAGG AGTGCCTGGC AGGCCCCTCA CCACCTCTGC CTACCTCA GTG AAG TTC      6130
                                                     Val Lys Phe
                                                     137

CCT TGT GGG AGG CCC TGG AAG CGG ATG GAG AAG AAG CGC AGT CAC CTG       6178
Pro Cys Gly Arg Pro Trp Lys Arg Met Glu Lys Lys Arg Ser His Leu

AAA CGA GAC ACA GAA GAC CAA GAA GAC CAA GTA GAT CCG CGG CTC ATT       6226
Lys Arg Asp Thr Glu Asp Gln Glu Asp Gln Val Asp Pro Arg Leu Ile

GAT GGG AAG ATG ACC AGG CGG GGA GAC AGC CCC TGG CAG GTGGGAGGCG        6275
Asp Gly Lys Met Thr Arg Arg Gly Asp Ser Pro Trp Gln
                                              184

AGGCAGCACC GGCTCGTCAC GTGCTGGGTC CGGGATCACT GAGTCCATCC TGGCAGCTAT     6335
GCTCAGGGTG CAGAAACCGA GAGGGAAGCG CTGCCATTGC GTTTGGGGGA TGATGAAGGT     6395
GGGGGATGCT TCAGGGAAAG ATGGACGCAA CCTGAGGGGA GAGGAGCAGC CAGGGTGGGT     6455
GAGGGGAGGG GCATGGGGGC ATGGAGGGGT CTGCAGGAGG GAGGGTTACA GTTTCTAAAA     6515
AGAGCTGGAA AGACACTGCT CTGCTGGCGG GATTTTAGGC AGAAGCCCTG CTGATGGGAG     6575
AGGGCTAGGA GGGAGGGCCG GGCCTGAGTA CCCCTCCAGC CTCCACATGG GAACTGACAC     6635
TTACTGGGTT CCCCTCTCTG CCAGGCATGG GGGAGATAGG AACCAACAAG TGGGAGTATT     6695
TGCCCTGGGG ACTCAGACTC TGCAAGGGTC AGGACCCCAA AGACCCGGCA GCCCAGTGGG     6755
ACCACAGCCA GGACGGCCCT TCAAGATAGG GGCTGAGGGA GGCCAAGGGG AACATCCAGG     6815
CAGCCTGGGG GCCACAAAGT CTTCCTGGAA GACACAAGGC CTGCCAAGCC TCTAAGGATG     6875
AGAGGAGCTC GCTGGGCGAT GTTGGTGTGG CTGAGGGTGA CTGAAACAGT ATGAACAGTG     6935
CAGGAACAGC ATGGGCAAAG GCAGGAAGAC ACCCTGGGAC AGGCTGACAC TGTAAAATGG     6995
GCAAAAATAG AAAACGCCAG AAAGGCCTAA GCCTATGCCC ATATGACCAG GGAACCCAGG     7055
AAAGTGCATA TGAAACCCAG GTGCCCTGGA CTGGAGGCTG TCAGGAGGCA GCCCTGTGAT     7115
GTCATCATCC CACCCCATTC CAG GTG GTC CTG CTG GAC TCA AAG AAG AAG        7165
                           Val Val Leu Leu Asp Ser Lys Lys Lys
                           185
```

FIG. 2F

```
CTG GCC TGC GGG GCA GTG CTC ATC CAC CCC TCC TGG GTG CTG ACA GCG         7213
Leu Ala Cys Gly Ala Val Leu Ile His Pro Ser Trp Val Leu Thr Ala

GCC CAC TGC ATG GAT GAG TCC AAG AAG CTC CTT GTC AGG CTT                 7255
Ala His Cys Met Asp Glu Ser Lys Lys Leu Leu Val Arg Leu
    O                                                 223
    ▼
GGTATGGGCT GGAGCCAGGC AGAAGGGGGC TGCCAGAGGC CTGGGTAGGG GGACCAGGCA       7315
GGCTGTTCAG GTTTGGGGGA CCCCGCTCCC CAGGTGCTTA AGCAAGAGGC TTCTTGAGCT       7375
CCACAGAAGG TGTTTGGGGG GAAGAGGCCT ATGTGCCCCC ACCCTGCCCA CCCATGTACA       7435
CCCAGTATTT TGCAGTAGGG GGTTCTCTGG TGCCCTCTTC GAATCTGGGC ACAGGTACCT       7495
GCACACACAT GTTTGTGAGG GGCTACACAG ACCTTCACCT CTCCACTCCC ACTCATGAGG       7555
AGCAGGCTGT GTGGGCCTCA GCACCCTTGG GTGCAGAGAC CAGCAAGGCC TGGCCTCAGG       7615
GCTGTGCCTC CCACAGACTG ACAGGGATGG AGCTGTACAG AGGGAGCCCT AGCATCTGCC       7675
AAAGCCACAA GCTGCTTCCC TAGCAGGCTG GGGGCTCCTA TGCATTGGCC CCGATCTATG       7735
GCAATTTCTG GAGGGGGGGT CTGGCTCAAC TCTTTCTGCC AAAAAGAAGG CAAAGCATAT       7795
TGAGAAAGGC CAAATTCACA TTTCCTACAG CATAATCTAT GCCAGTGGCC CCGTGGGGCT       7855
TGGCTTAGAA TTCCCAGGTG CTCTTCCCAG GGAACCATCA GTCTGGACTG AGAGGACCTT       7915
CTCTCTCAGG TGGGACCCGG CCCTGTCCTC CCTGGCAGTG CCGTGTTCTG GGGGTCCTCC       7975
TCTCTGGGTC TCACTGCCCC TGGGGTCTCT CCAGCTACCT TTGCTCCATG TTCCTTTGTG       8035
GCTCTGGTCT GTGTCTGGGG TTTCCAGGGG TCTCGGGCTT CCCTGCTGCC CATTCCTTCT       8095
CTGGTCTCAC GGCTCCGTGA CTCCTGAAAA CCAACCAGCA TCCTACCCCT TTGGATTGAC       8155
ACCTGTTGGC CACTCCTTCT GGCAGGAAAA GTCACCGTTG ATAGGGTTCC ACGGCATAGA       8215
CAGGTGGCTC CGCGCCAGTG CCTGGGACGT GTGGGTGCAC AGTCTCCGGG TGAACCTTCT       8275
TCAGGCCCTC TCCCAGGCCT GCAGGGGCAC ACCAGTGGGT GGGCCTCAGG AAAGTGCCAC       8335
                                                         ▼
TGGGGAGAGG CTCCCCGCAG CCCACTCTGA CTGTGCCCTC TGCCCTGCA GGA GAG           8390
                                                         Gly Glu
                                                         224

TAT GAC CTG CGG CGC TGG GAG AAG TGG GAG CTG GAC CTG GAC ATC AAG         8438
Tyr Asp Leu Arg Arg Trp Glu Lys Trp Glu Leu Asp Leu Asp Ile Lys
```

*FIG. 2G*

```
GAG GTC TTC GTC CAC CCC AAC TAC AGC AAG AGC ACC ACC GAC AAT GAC         8486
Glu Val Phe Val His Pro Asn Tyr Ser Lys Ser Thr Thr Asp Asn Asp
                        ◆                                   ○

ATC GCA CTG CTG CAC CTG GCC CAG CCC GCC ACC CTC TCG CAG ACC ATA         8534
Ile Ala Leu Leu His Leu Ala Gln Pro Ala Thr Leu Ser Gln Thr Ile

GTG CCC ATC TGC CTC CCG GAC AGC GGC CTT GCA GAG CGC GAG CTC AAT         8582
Val Pro Ile Cys Leu Pro Asp Ser Gly Leu Ala Glu Arg Glu Leu Asn

CAG GCC GGC CAG GAG ACC CTC GTG ACG GGC TGG GGC TAC CAC AGC AGC         8630
Gln Ala Gly Gln Glu Thr Leu Val Thr Gly Trp Gly Tyr His Ser Ser

CGA GAG AAG GAG GCC AAG AGA AAC CGC ACC TTC GTC CTC AAC TTC ATC         8678
Arg Glu Lys Glu Ala Lys Arg Asn Arg Thr Phe Val Leu Asn Phe Ile

AAG ATT CCC GTG GTC CCG CAC AAT GAG TGC AGC GAG GTC ATG AGC AAC         8726
Lys Ile Pro Val Val Pro His Asn Glu Cys Ser Glu Val Met Ser Asn

ATG GTG TCT GAG AAC ATG CTG TGT GCG GGC ATC CTC GGG GAC CGG CAG         8774
Met Val Ser Glu Asn Met Leu Cys Ala Gly Ile Leu Gly Asp Arg Gln

GAT GCC TGC GAG GGC GAC AGT GGG GGG CCC ATG GTC GCC TCC TTC CAC         8822
Asp Ala Cys Glu Gly Asp Ser Gly Gly Pro Met Val Ala Ser Phe His

GGC ACC TGG TTC CTG GTG GGC CTG GTG AGC TGG GGT GAG GGC TGT GGG         8870
Gly Thr Trp Phe Leu Val Gly Leu Val Ser Trp Gly Glu Gly Cys Gly

CTC CTT CAC AAC TAC GGC GTT TAC ACC AAA GTC AGC CGC TAC CTC GAC         8918
Leu Leu His Asn Tyr Gly Val Tyr Thr Lys Val Ser Arg Tyr Leu Asp

TGG ATC CAT GGG CAC ATC AGA GAC AAG GAA GCC CCC CAG AAG AGC TGG         8966
Trp Ile His Gly His Ile Arg Asp Lys Glu Ala Pro Gln Lys Ser Trp

GCA CCT TAG CGACCCTCCC TGCAGGGCTG GGCTTTTGCA TGGCAATGGA                 9015
Ala Pro Stop
       419

TGGGACATTA AAGGGACATG TAACAAGCAC ACCGGCCTGC TGTTCTGTCC TTCCATCCCT       9075

CTTTTGGGCT CTTCTGGAGG GAAGTAACAT TTACTGAGCA CCTGTTGTAT GTCACATGCC       9135

TTATGAATAG AATCTTAACT CCTAGAGCAA CTCTGTGGGG TGGGGAGGAG CAGATCCAAG       9195
```

*FIG. 2H*

```
TTTTGCGGGG TCTAAAGCTG TGTGTGTTGA GGGGGATACT CTGTTTATGA AAAAGAATAA    9255
AAAACACAAC CACGAAGCCA CTAGAGCCTT TTCCAGGGCT TTGGGAAGAG CCTGTGCAAG    9315
CCGGGGATGC TGAAGGTGAG GCTTGACCAG CTTTCCAGCT AGCCCAGCTA TGAGGTAGAC    9375
ATGTTTAGCT CATATCACAG AGGAGGAAAC TGAGGGGTCT GAAAGGTTTA CATGGTGGAG    9435
CCAGGATTCA AATCTAGGTC TGACTCCAAA ACCCAGGTGC TTTTTTCTGT TCTCCACTGT    9495
CCTGGAGGAC AGCTGTTTCG ACGGTGCTCA GTGTGGAGGC CACTATTAGC TCTGTAGGGA    9555
AGCAGCCAGA GACCCAGAAA GTGTTGGTTC AGCCCAGAAT                          9595
```

*FIG. 2I*

|                                                             |      |
|-------------------------------------------------------------|------|
| CGG CGA ACT                                                 | -42  |
| TGG AGT ATC TCC ACG ACC CCC CCC TGT GCC AGT CCC TCC AGA ATG TGG |  6   |
|                                                     Met Trp    |      |
|                                                     -42        |      |
| CAG CTC ACA AGC CTC CTG CTG TTC GTG GCC ACC TGG GGA ATT TCC GGC | 54   |
| Gln Leu Thr Ser Leu Leu Leu Phe Val Ala Thr Trp Gly Ile Ser Gly |      |
| -40                                  -30                        |      |
| ACA CCA GCT CCT CTT GAC TCA GTG TTC TCC AGC AGC GAG CGT GCC CAC | 102  |
| Thr Pro Ala Pro Leu Asp Ser Val Phe Ser Ser Ser Glu Arg Ala His |      |
|                 -20                                    -10      |      |
| CAG GTG CTG CGG ATC CGC AAA CGT GCC AAC TCC TTC CTG GAG GAG CTC | 150  |
| Gln Val Leu Arg Ile Arg Lys Arg Ala Asn Ser Phe Leu Glu Glu Leu |      |
|                         -1 +1                                   |      |
| CGT CAC AGC AGC CTG GAG CGG GAG TGC ATA GAG GAG ATC TGT GAC TTC | 198  |
| Arg His Ser Ser Leu Glu Arg Glu Cys Ile Glu Glu Ile Cys Asp Phe |      |
|         10                                  20                  |      |
| GAG GAG GCC AAG GAA ATT TTC CAA AAT GTG GAT GAC ACA CTG GCC TTC | 246  |
| Glu Glu Ala Lys Glu Ile Phe Gln Asn Val Asp Asp Thr Leu Ala Phe |      |
|                     30                                    40    |      |
| TGG TCC AAG CAC GTC GAC GGT GAC CAG TGC TTG GTC TTG CCC TTG GAG | 294  |
| Trp Ser Lys His Val Asp Gly Asp Gln Cys Leu Val Leu Pro Leu Glu |      |
|                                 50                              |      |
| CAC CCG TGC GCC AGC CTG TGC TGC GGG CAC GGC ACG TGC ATC GAC GGC | 342  |
| His Pro Cys Ala Ser Leu Cys Cys Gly His Gly Thr Cys Ile Asp Gly |      |
|             60                                  70              |      |
| ATC GGC AGC TTC AGC TGC GAC TGC CGC AGC GGC TGG GAG GGC CGC TTC | 390  |
| Ile Gly Ser Phe Ser Cys Asp Cys Arg Ser Gly Trp Glu Gly Arg Phe |      |
|                         80                                      |      |
| TGC CAG CGC GAG GTG AGC TTC CTC AAT TGC TCT CTG GAC AAC GGC GGC | 438  |
| Cys Gln Arg Glu Val Ser Phe Leu Asn Cys Ser Leu Asp Asn Gly Gly |      |
|     90                           ✦            100               |      |
| TGC ACG CAT TAC TGC CTA GAG GAG GTG GGC TGG CGG CGC TGT AGC TGT | 486  |
| Cys Thr His Tyr Cys Leu Glu Glu Val Gly Trp Arg Arg Cys Ser Cys |      |
|                         110                                120  |      |
| GCG CCT GGC TAC AAG CTG GGG GAC GAC CTC CTG CAG TGT CAC CCC GCA | 534  |
| Ala Pro Gly Tyr Lys Leu Gly Asp Asp Leu Leu Gln Cys His Pro Ala |      |
|                                     130                         |      |
| GTG AAG TTC CCT TGT GGG AGG CCC TGG AAG CGG ATG GAG AAG AAG CGC | 582  |
| Val Lys Phe Pro Cys Gly Arg Pro Trp Lys Arg Met Glu Lys Lys Arg |      |
|             140                                    150          |      |

FIG. 3A

```
AGT CAC CTG AAA CGA GAC ACA GAA GAC CAA GAA GAC CAA GTA GAT CCG      630
Ser His Leu Lys Arg Asp Thr Glu Asp Gln Glu Asp Gln Val Asp Pro
                    160

CGG CTC ATT GAT GGG AAG ATG ACC AGG CGG GGA GAC AGC CCC TGG CAG      678
Arg Leu Ile Asp Gly Lys Met Thr Arg Arg Gly Asp Ser Pro Trp Gln
    170                                         180

GTG GTC CTG CTG GAC TCA AAG AAG AAG CTG GCC TGC GGG GCA GTG CTC      726
Val Val Leu Leu Asp Ser Lys Lys Lys Leu Ala Cys Gly Ala Val Leu
                    190                                     200

ATC CAC CCC TCC TGG GTG CTG ACA GCG GCC CAC TGC ATG GAC GAG TCC      774
Ile His Pro Ser Trp Val Leu Thr Ala Ala His Cys Met Asp Glu Ser
                                    210

AAG AAG CTC CTT GTC AGG CTT GGA GAG TAT GAC CTG CGG CGC TGG GAG      822
Lys Lys Leu Leu Val Arg Leu Gly Glu Tyr Asp Leu Arg Arg Trp Glu
                220                                 230

AAG TGG GAG CTG GAC CTG GAC ATC AAG GAG GTC TTC GTC CAC CCC AAC      870
Lys Trp Glu Leu Asp Leu Asp Ile Lys Glu Val Phe Val His Pro Asn
                            240

TAC AGC AAG AGC ACC ACC GAC AAT GAC ATC GCA CTG CTG CAC CTG GCC      918
Tyr Ser Lys Ser Thr Thr Asp Asn Asp Ile Ala Leu Leu His Leu Ala
        250                                 260

CAG CCC GCC ACC CTC TCG CAG ACC ATA GTG CCC ATC TGC CTC CCG GAC      966
Gln Pro Ala Thr Leu Ser Gln Thr Ile Val Pro Ile Cys Leu Pro Asp
                    270                                     280

AGC GGC CTT GCA GAG CGC GAG CTC AAT CAG GCC GGC CAG GAG ACC CTC     1014
Ser Gly Leu Ala Glu Arg Glu Leu Asn Gln Ala Gly Gln Glu Thr Leu
                                290

GTG ACG GGC TGG GGC TAC CAC AGC AGC CGA GAG AAG GAG GCC AAG AGA     1062
Val Thr Gly Trp Gly Tyr His Ser Ser Arg Glu Lys Glu Ala Lys Arg
            300                                 310

AAC CGC ACC TTC GTC CTC AAC TTC ATC AAG ATT CCC GTG GTC CCG CAC     1110
Asn Arg Thr Phe Val Leu Asn Phe Ile Lys Ile Pro Val Val Pro His
                            320

AAT GAG TGC AGC GAG GTC ATG AGC AAC ATG GTG TCT GAG AAC ATG CTG     1158
Asn Glu Cys Ser Glu Val Met Ser Asn Met Val Ser Glu Asn Met Leu
    330                                         340

TGT GCG GGC ATC CTC GGG GAC CGG CAG GAT GCC TGC GAG GGC GAC AGT     1206
Cys Ala Gly Ile Leu Gly Asp Arg Gln Asp Ala Cys Glu Gly Asp Ser
                    350                                     360

GGG GGG CCC ATG GTC GCC TCC TTC CAC GGC ACC TGG TTC CTG GTG GGC     1254
Gly Gly Pro Met Val Ala Ser Phe His Gly Thr Trp Phe Leu Val Gly
                            370
```

*FIG. 3B*

```
CTG GTG AGC TGG GGT GAG GGC TGT GGG CTC CTT CAC AAC TAC GGC GTT            1302
Leu Val Ser Trp Gly Glu Gly Cys Gly Leu Leu His Asn Tyr Gly Val
            380                                     390

TAC ACC AAA GTC AGC CGC TAC CTC GAC TGG ATC CAT GGG CAC ATC AGA            1350
Tyr Thr Lys Val Ser Arg Tyr Leu Asp Trp Ile His Gly His Ile Arg
                                400

GAC AAG GAA GCC CCC CAG AAG AGC TGG GCA CCT TAG CGA CCC TCC CTG            1398
Asp Lys Glu Ala Pro Gln Lys Ser Trp Ala Pro Stop
    410                                 419

CAG GGC TGG GCT TTT GCA TGG CAA TGG ATG GGA CAT TAA AGG GAC ATG            1446

TAA CAA GCA CAC CGG CCT GCT GTT CTG TCC TTC CAT CCC TCT TTT GGG            1494

CTC TTC TGG AGG GAA GTA ACA TTT ACT GAG CAC CTG TTG TAT GTC ACA            1542

TGC CTT ATG AAT AGA ATC TTA ACT CCT AGA GCA ACT CTG TGG GGT GGG            1590

GAG GAG CAG ATC CAA GTT TTG CGG GGT CTA AAG CTG TGT GTG TTG AGG            1638

GGG ATA CTC TGT TTA TGA AAA ACA ATA AAA AAC ACA ACC ACG AAA AAA            1686

AAA                                                                         1689
```

*FIG. 3C*

PLASMID CODING FOR HUMAN PROTEIN C

CROSS-REFERENCE TO RELATED APPLICATION

This application is a continuation of U.S. application Ser. No. 06/766,109 filed Aug. 15, 1985, now U.S. Pat. No. 4,968,626.

TECHNICAL FIELD

The present invention relates to sequences coding for plasma proteins in general and, more specifically, to a DNA sequence which codes for a protein having substantially the same structure and/or activity of human protein C.

BACKGROUND ART

Protein C is a zymogen, or precursor, of a serine protease which plays an important role in the regulation of blood coagulation and generation of fibrinolytic activity in vivo. It is synthesized in the liver as a single-chain polypeptide which undergoes considerable processing to give rise to a two-chain molecule comprising heavy (Mr=40,000) and light (Mr=21,000) chains held together by disuldhide bonds. The circulating two-chain intermediate is converted to the biologically active form of the molecule, known as "activated protein C" (APC), by the thrombin-mediated cleavage of a 12-residue peptide from the amino-terminus of the heavy chain. The cleavage reaction is augmented in vivo by thrombomodulin, an endothelial cell cofactor (Esmon and Owen, Proc. Natl. Acad. Sci. USA 78: 2249-2252, 1981).

Protein C is a vitamin K-dependent glycoprotein which contains approximately eleven residues of gamma-carboxyglutamic acid (gla) and one equivalent of beta-hydroxyaspartic acid which are formed by post-translational modifications of glutamic acid and aspartic acid residues, respectively. The post-translational formation of specific gamma-carboxyglutamic acid residues in protein C requires vitamin K. These unusual amino acid residues bind to calcium ions and are believed to be responsible for the interaction of the protein with phospholipid, which is required for the anticoagulant activity of protein C.

In contrast to the coagulation-promoting action of other vitamin K-dependent plasma proteins, such as factor VII, factor IX, and factor X, activated protein C acts as a regulator of the coagulation process through the inactivation of factor Va and factor VIIIa by limited proteolysis. The inactivation of factors Va and VIIIa by protein C is dependent upon the presence of acidic phospholipids and calcium ions. Protein S has been reported to regulate this activity by accelerating the APC-catalyzed proteolysis of factor Va (Walker, J. Biol. Chem. 255: 5521-5524, 1980).

Protein C has also been implicated in the action of plasminogen activator (Kisiel and Fujikawa, Behring Inst. Mitt. 73: 29-42, 1983). Infusion of bovine APC into dogs results in increased plasminogen activator activity (Comp and Esmon, J. Clin. Invest. 68: 1221-1228, 1981) Recent studies (Sakata et al., Proc. Natl. Acad. Sci. USA 82: 1121-1125, 1985) have shown that addition of APC to cultured endothelial cells leads to a rapid, dose-dependent increase in fibrinolytic activity in the conditioned media, reflecting increases in the activity of both urokinase-related and tissue-type plasminogen activators by the cells. APC treatment also results in a dose-dependent decrease in antiactivator activity.

Inherited protein C deficiency is associated with recurrent thrombotic disease (Broekmans et al., New Eng. J. Med. 309: 340-344, 1983; and Seligsohn et al. New Eng. J. Med. 310: 559-562, 1984) and may result from genetic disorder or from trauma, such as liver disease or surgery. This condition is generally treated with oral anticoagulants. Beneficial effects have also been obtained through the infusion of protein C-containing normal plasma (see Gardiner and Griffin in Prog. in Hematology, ed. Brown, Grune & Stratton, NY, 13: 265-278). In addition, some investigators have discovered that the anti-coagulant activity of protein C is useful in treating thrombotic disorders, such as venous thrombosis (WO 85/00521). In some parts of the world, it is estimated that approximately 1 in 16,000 individuals exhibit protein C deficiency. Further, a total deficiency in protein C is fatal in newborns.

While natural protein C may be purified from clotting factor concentrates (Marlar et al., Blood 59: 1067-1072) or from plasma (Kisiel, ibid), it is a complex and expensive process, in part due to the limited availability of the starting material and the low concentration of protein C in plasma. Furthermore, the therapeutic use of products derived from human blood carries the risk of disease transmission by, for example, hepatitis virus, cytomegalovirus, or the causative agent of acquired immune deficiency syndrome (AIDS). In view of protein C's clinical applicability in the treatment of thrombotic disorders, the production of useful quantities of protein C and activated protein C is clearly invaluable.

DISCLOSURE OF INVENTION

Briefly stated, the present invention discloses a DNA sequence which codes for a protein having substantially the same biological activity as human protein C.

In addition, the present invention discloses a recombinant plasmid or bacteriophage transfer vector comprising a cDNA sequence comprising the protein C gene cDNA sequence. The amino acid and DNA sequences of this cDNA coding for human protein C are also disclosed.

Other aspects of the invention will become evident upon reference to the detailed description and attached drawings.

BRIEF DESCRIPTION OF THE DRAWINGS

FIGS. 2A-2I illustrates the complete genomic sequence, including exons and introns for human protein C. Arrowheads indicate intron-exon splice junctions. The polyadenylation or processing sequences of A-T-T-A-A-A and A-A-T-A-A-A at the 3' end are boxed. , potential carbohydrate binding sites; ↓, apparent cleavage sites for processing of the connecting dipeptide; ↓, site of cleavage in the heavy chain when protein C is converted to activated protein C; •, sites of polyadenylation.

FIGS. 3A-3C depict the amino acid and DNA sequences for a cDNA coding for human protein C.

FIG. 4 illustrates a proposed model for the structure of human protein C.

BEST MODE FOR CARRYING OUT THE INVENTION

Figure 1:
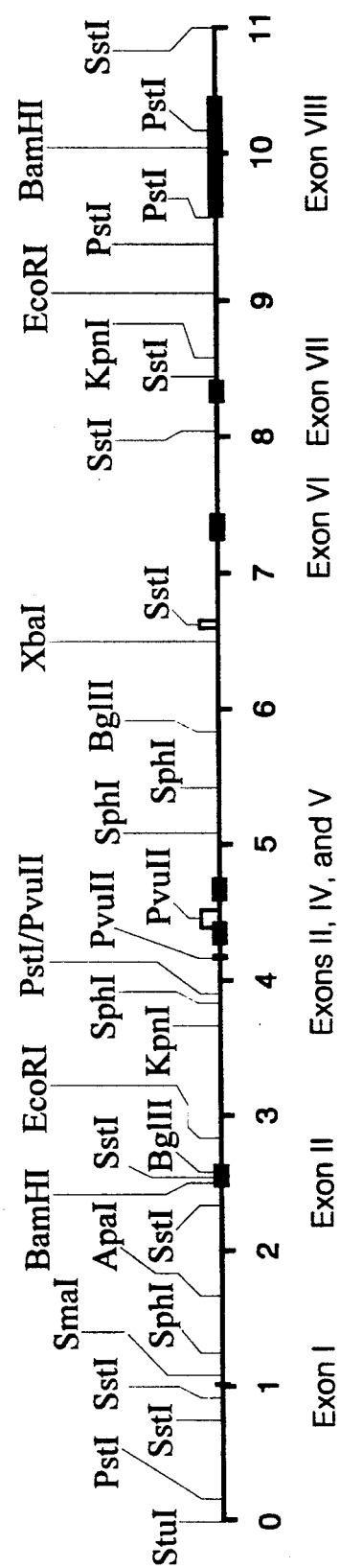
FIG. 1 illustrates a restriction enzyme map of the genomic DNA coding for human protein C.

Prior to setting forth the invention, it may be helpful to an understanding thereof to set forth definitions of certain terms to be used hereinafter.

Biological Activity: A function or set of functions performed by a molecule in a biological context (i.e., in an organism or an in vitro facsimile). Biological activities of proteins may be divided into catalytic and effector activities. Catalytic activities of the vitamin K-dependent plasma proteins generally involve the specific proteolytic cleavage of other plasma proteins, resulting in activation or deactivation of the substrate. Emector activities include specific binding of the biologically active molecule to calcium or other small molecules, to macromolecules, such as proteins, or to cells. Effector activity frequently augments, or is essential to, catalytic activity under physiological conditions.

For protein C, biological activity is characterized by its anticoagulant and fibrinolytic properties. Protein C, when activated, inactivates factor Va and factor VIIIA in the presence of phospholipid and calcium. Protein S appears to be involved in the regulation of this function (Walker, ibid). Activated protein C also enhances fibrinolysis, an effect believed to be mediated by the lowering of levels of plasminogen activator inhibitors (van Hinsbergh et al., *Blood* 63: 444-451, 1985). As more fully described below, Exons VII and VIII are primarily responsible for the catalytic activity of protein C.

Transfer Vector: A DNA molecule which contains, inter alia, genetic information which ensures its own replication when transferred to a host microorganism strain. Examples of transfer vectors commonly used for recombinant DNA are plasmids and certain bacteriophages. Transfer vectors normally include an origin of replication and sequences necessary for efficient transcription and translation of DNA.

As noted above, protein C is synthesized as a single-chain polypeptide which undergoes considerable processing to give rise to a two-chain molecule; a heavy chain ($M_r$ 41,000) and a light chain ($M_r$ 21,000 held together by a disulfide bond.

Within the present invention, a λgt11 cDNA library was prepared from human liver mRNA. This library was then screened with $^{125}$I labeled antibody to human protein C. Antibody-reactive clones were further analyzed for the synthesis of a fusion protein of B-galactosidase and protein C in the λgt11 vector.

One of the clones gave a strong signal with the antibody probe and was found to contain an insert of approximately 1400 bp. DNA sequence analysis of the DNA insert revealed a predicted amino acid sequence which shows a high degree of homology to major portions of the bovine protein C, as determined by Fernlund and Stenflo (*J. Biol. Chem.* 257: 12170-12179; *J. Biol. Chem.* 257: 12180-12190).

The DNA insert contained the majority of the coding region for protein C beginning with amino acid 65 of the light chain, including the entire heavy chain coding region, and proceeding to the termination codon. Further, following the stop codon of the heavy chain, there are 294 base pairs of 3' noncoding sequence and a Doly (A) tail of 9 base pairs. The processing or polyadenylation signal A-A-T-A-A-A was present 13 base pairs upstream from the poly (A) tail in this cDNA insert. This sequence is one of two potential polyadenylation sites.

The cDNA sequence also contains the dipeptide Lys-Arg at position 156-157, which separates the light chain from the heavy chain and is removed during processing by proteolytic cleavage. Upon activation by thrombin, the heavy chain of human protein C is cleaved between arginine-12 and leucine-13, releasing the activation peptide.

In order to obtain the remainder of the light chain coding sequence (amino acids 1-64), a human genomic library in λ Charon 4A phage was screened for genomic clones of human protein C using the cDNA described above as a hybridization probe. Three different λ Charon 4A phage were isolated that contained overlapping inserts for the gene coding for protein C.

The position of exons on the three phage clones were determined by Southern blot hybridization of digests of these clones with probes made from the 1400 bp cDNA described above. The genomic DNA inserts in these clones were mapped by single and double restriction enzyme digestion followed by agarose gel electrophoresis, Southern blotting, and hybridization to radiolabeled 5' and 3' probes derived from the cDNA for human protein C, as shown in FIG. 1.

DNA sequencing studies were performed using the dideoxy chain-termination method. As shown in FIG. 2, the nucleotide sequence for the gene for human protein C spans approximately 11 kb of DNA. These studies further revealed a potential pre-oro leader sequence of 42 amino acids. Based on homology with the leader sequence of bovine protein C in the region $-1$ to $-20$, it is likely that the pre-pro leader sequence is cleaved by a signal peptidase following the Ala residue at position $-10$. Processing to the mature protein involves additional proteolytic cleavage following residue $-1$ to remove the amino-terminal propeptide, and at residues 155 and 157 to remove the Lys-Arg dipeptide which connects the light and heavy chains. This final processing yields a light chain of 155 amino acids and a heavy chain of 262 amino acids.

As noted above, the protein C gene is composed of eight exons ranging in size from 25 to 885 nucleotides, and seven introns ranging in size from 92 to 2668 nucleotides. Exon I and a portion of Exon II code for the 42 amino acid pre-pro peptide. The remaining portion of Exon II, Exon III, Exon IV, Exon V, and a portion of Exon VI code for the light chain of protein C. The remaining portion of Exon VI, Exon VII, and Exon VIII code for the heavy chain of protein C. The amino acid and DNA sequences for a cDNA coding for human protein C are shown in FIG. 3.

The location of the introns in the gene for protein C are primarily between various functional domains. Exon II spans the highly conserved region of the leader sequence and the gamma-carboxyglutamic acid (gla) domain. Exon III includes a stretch of eight amino acids which connect the Gla and growth factor domains. Exons IV and V each represent a potential growth factor domain, while Exon VI covers a connecting region which includes the activation peptide. Exons VII and VIII cover the catalytic domain typical of all serine proteases.

The amino acid sequence and tentative structure for human prepro protein C are shown in FIG. 4. Protein C is shown without the Lys-Arg dipeptide, which connects the light and heavy chains. The location of the seven introns (A through G) is indicated by solid bars. Amino acids flanking known proteolytic cleavage sites are circled. designates potential carbohydrate binding sites. The first amino acid in the light chain, activation peptide, and heavy chain start with number 1, and differ from that shown in FIGS. 2 and 3.

Carbohydrate attachment sites are located at residue 97 in the light chain and residues 79, 144, and 160 in the heavy chain, according to the numbering scheme of FIG. 4. The carbohydrate moiety is covalently linked to Asn, but Thr, Ser, or Gln may be substituted. In the majority of instances, the carbohydrate attachment environment can be represented by N-X-Ser or N-X-Thr, where N=Asn, Thr, Ser, or Gln, and X=any amino acid.

The catalytic domain of protein C, which is encoded by Exons VII and VIII, plays a regulatory role in the coagulation process. This domain possesses serine protease activity which specifically cleaves certain plasma proteins (i.e., factors Va and VIIIa), resulting in their activation or deactivation. As a result of this selective proteolysis, protein C displays anticoagulant and fibrinolytic activities.

The example which follows describes the cloning of DNA sequences encoding human protein C.

EXAMPLE

Restriction endonucleases and other DNA modification enzymes (e.g., $T_4$ polynucleotide kinase, bacterial alkaline phosphatase, Klenow DNA polymerase, $T_4$ polynucleotide ligase) may be obtained from Bethesda Research Laboratories (BRL) and New England Biolabs and are used as directed by the manufacturer, unless otherwise noted.

CLONING OF DNA SEQUENCES ENCODING HUMAN PROTEIN C

A cDNA coding for a portion of human protein C was prepared as described by Foster and Davie (PNAS (USA) 81: 4766-4770, 1984, herein incorporated by reference). Briefly, a λgt11 cDNA library was prepared from human liver mRNA by conventional methods. Clones were screened using $^{125}$I-labeled affinity-purified antibody to human protein C, and phage were prepared from positive clones by the plate lysate method (Maniatis et al., ibid), followed by banding on a cesium chloride gradient. The cDNA inserts were removed using Eco RI and subcloned into plasmid pUC9 (Vieira and Messing, *Gene* 19: 259-268, 1982). Restriction fragments were subcloned in the phage vectors M13mp10 and m13mp11 (Messing, *Meth. in Enzymology* 101: 20-77, 1983) and sequenced by the dideoxy method (Sanger et al., *Proc. Natl. Acad. Sci. USA* 74: 5463-5467, 1977). A clone was selected which contained DNA corresponding to the known sequence of human protein C (Kisiel, ibid) and encoded protein C beginning at amino acid 65 of the light chain and extending through the heavy chain and into the 3' non-coding region. This clone was designated λHC1375.

The cDNA insert from λHC1375 was nick translated using ($\alpha-^{32}$P dNTP's and used to probe a human genomic library in phage λ Charon 4A (Maniatis et al., *Cell* 15: 687-702, 1978) using the plaque hybridization procedure of Benton and Davis (*Science* 196: 181-182, 1977) as modified by Woo (*Meth. in Enzymology* 68: 381-395, 1979). Positive clones were isolated and plaque-purified (by Foster et al., PNAS (USA) 82: 4673-4677, 1985, herein incorporated by reference).

Phage DNA was prepared from positive clones by the method of Silhavy et al. (Experiments with Gene Fusion, Cold Spring Harbor Laboratory, 1984). The purified phage DNA was digested with EcoRI and subcloned into pUC9 for further mapping and sequencing studies. Further analysis suggested that the gene for protein C was present in three EcoRI fragments. In order to generate overlapping protein C DNA sequences, purified phage DNA was digested with Bgl II and subcloned into pUC9.

The sequences of the EcoRI and Bgl II protein C fragments were determined by subcloning the fragments into M13 phage cloning vectors. Sequence analysis of the overlapping fragments established the DNA sequence of the entire protein C gene.

Alternatively, the complete DNA sequence has been determined using a second cDNA clone isolated from a λgt11 cDNA library. This clone encodes a major portion of protein C, beginning at amino acid 24 and including the heavy chain coding region, termination codon, and 3' noncoding region. The insert from this λphage clone was subcloned into pUC9 and the resultant plasmid designated pHC 6L.

This PHC 6L insert was nick translated and used to probe a human genomic library in phage λCharon 4A. One genomic clone was identified which contained a 4.4 kb EcoRI fragment corresponding to the 5' end of the protein C gene. This phage clone was subcloned into pUC9 and the resultant plasmid designated pHCR 4.4. DNA sequence analysis revealed that the pHCR 4.4 insert comprised two exons, encoding amino acids −42 to −19, and amino acids −19 to 37. Thus, the DNA sequence of the entire protein C gene was established due to the overlapping sequences of pHC 6L (24 to 3' noncoding region) and pHCR 4.4 (−42 to 37).

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A bacterial plasmid or bacteriophage transfer vector comprising cDNA coding for the amino acid sequence of FIG. 3, starting with alanine, number 1, and ending with proline, number 419, said cDNA sequence coding for human protein C.

2. The plasmid or transfer vector of claim 1, further comprising cDNA coding for the amino acid sequence of FIG. 3, starting with methionine, number −42, and ending with arginine, number −1.

3. The plasmid or transfer vector of claim 1, comprising the cDNA sequence of FIG. 3, from bp 127 to bp 1383.

4. The plasmid or transfer vector of claim 2, comprising the cDNA sequence of FIG. 3, from bp 1 to bp 1383.

* * * * *

UNITED STATES PATENT AND TRADEMARK OFFICE
CERTIFICATE OF CORRECTION

PATENT NO. : 5,302,529
DATED : April 12, 1994
INVENTOR(S) : Donald C. Foster, et. al.

It is certified that error appears in the above-indentified patent and that said Letters Patent is hereby corrected as shown below:

At column 1 following the title, please add the following:

--GOVERNMENT SUPPORT

This invention was made with government support under National Institutes of Health grant number HL16919. The government has certain rights in the invention.--

Signed and Sealed this

Tenth Day of April, 2001

Attest:

NICHOLAS P. GODICI

Attesting Officer

Acting Director of the United States Patent and Trademark Office